United States Patent [19]

Gravisse et al.

[11] Patent Number: 4,874,188

[45] Date of Patent: Oct. 17, 1989

[54] FIDUCIARY OR SECURITY OBJECT ENABLING VISUAL OR OPTICAL AUTHENTIFICATION

[75] Inventors: Philippe Gravisse, Paris; Jacques Duchateau, Recquignies; Maurice Perron, Viroflay, all of France

[73] Assignee: B.R.I.C.-Bureau de Recherche pour l' Innovation et la Convergence & Banque de France, Paris, France

[21] Appl. No.: 105,741

[22] Filed: Oct. 8, 1987

[30] Foreign Application Priority Data

Oct. 10, 1986 [FR] France ................................ 86 14161

[51] Int. Cl.$^4$ .............................................. B42D 15/00
[52] U.S. Cl. ........................................ 283/89; 283/91; 283/74; 252/301.33
[58] Field of Search ................. 283/74, 89, 91; 427/7; 428/916; 252/301.33

[56] References Cited

U.S. PATENT DOCUMENTS

| | | | |
|---|---|---|---|
| 4,161,388 | 7/1979 | Bouchard et al. | 431/359 |
| 4,208,300 | 6/1980 | Grauisse | 252/301.33 |
| 4,442,170 | 4/1984 | Kaule et al. | 283/92 |
| 4,451,530 | 5/1984 | Kaule et al. | 283/92 |
| 4,500,116 | 2/1985 | Ferro et al. | 283/92 |
| 4,705,300 | 11/1987 | Berning et al. | 283/91 |

FOREIGN PATENT DOCUMENTS 2016370 9/1979 United Kingdom .
1561530 2/1980 United Kingdom .

*Primary Examiner*—John F. Niebling
*Assistant Examiner*—Steven P. Marquis
*Attorney, Agent, or Firm*—Sughrue, Mion, Zinn, Macpeak & Seas

[57] ABSTRACT

The present invention relates to the authentication of fiduciary or security objects, such as official documents, contracts, banknotes, credit cards and computer diskettes.

The object to be authenticated is marked with a matrix composed of an organic resin of the vinyl or acrylic type, or any other similar resin, incorporating a series of sparkling doping materials and a series of photoluminescent doping materials with long-lasting remanence.

This marking is carried out by coating, transfer of a film, printing, or integration of particles into the fiduciary material. The document marked in this manner can, in addition, be covered with a substance which is transparent in the visible spectrum going from UV to IR with the exception of a given wavelength band.

The object marked in accordance with the invention has a first color in daylight, a second color when it is submitted to ultraviolet radiation and a third color from long-lasting when it is placed in darkness.

15 Claims, 1 Drawing Sheet

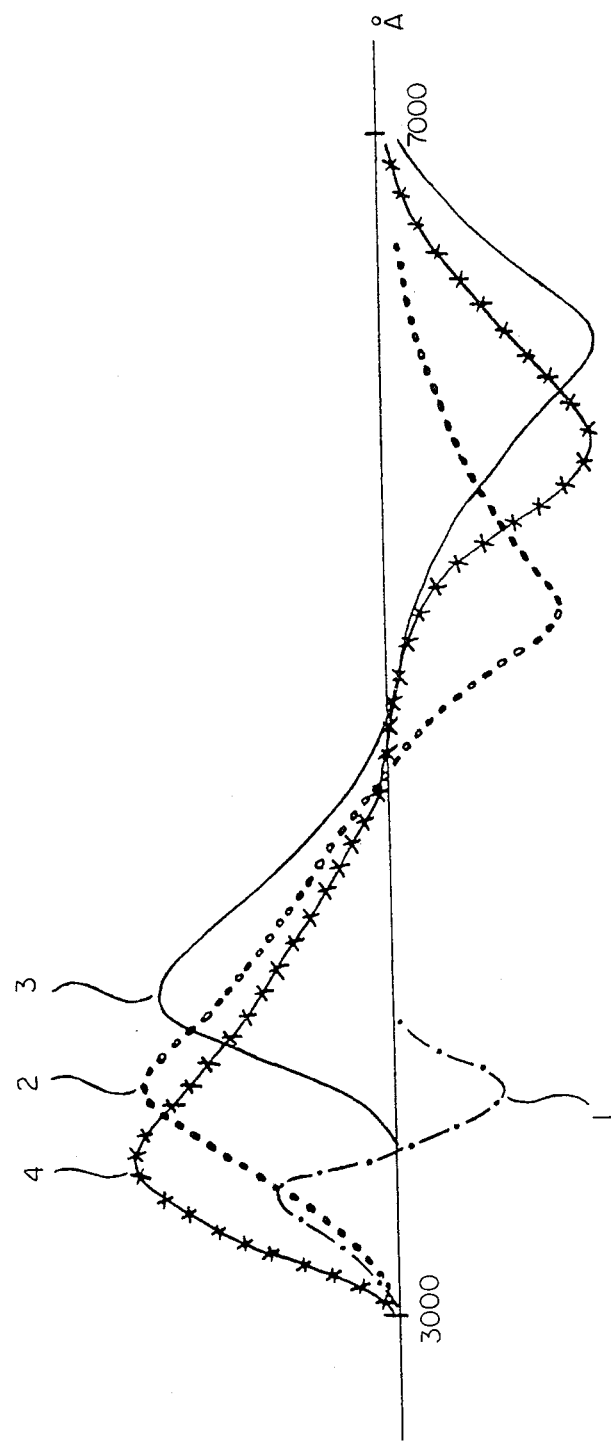

FIDUCIARY OR SECURITY OBJECT ENABLING VISUAL OR OPTICAL AUTHENTIFICATION

The present invention relates to fiduciary or security objects having optical characteristics which enable their authentication and which render their imitation difficult.

Numerous objects have a legal or economic value of great importance and their reproduction by forgers creates serious consequences for the issuing authority or the community. Legal documents, therefore, are for example official documents, contracts, certificates or various titles; economic documents are securities, banknotes, credit cards, computer program diskettes; and in general any object whose authentication is important.

The state-of-the-art technique which has been proposed is to mark the objects with a fluorescent material. The verification of the authenticity is carried out by exposing the object to ultraviolet radiation and by examining the color of the part of the marked document. This technique does not, however, offer adequate security since, by using simple means of analysis of the re-emitted color, the type of fluorescent material used can be determined and the the marked object can be reproduced.

The object of the present invention is to overcome this disadvantage by providing a marking using a matrix incorporating a series of sparkling doping materials with short remanence and a series of photoluminescent doping materials with long-lasting remanence which form a light cascade.

The objects marked in accordance with the invention show a first color in daylight, a second color, which is different from the first, when they are submitted to an ultraviolet light source, and a third color when said object is placed in darkness.

BRIEF DESCRIPTION OF THE DRAWINGS

FIG. 1 is a graph of radiation absorption and radiation re-emission characteristics of a light cascade of an example forming an embodiment of the invention.

The organic matrix in which the doping materials are incorporated is composed by a synthesis binder whose spectral band goes from the ultraviolet to the close infrared. It can be produced in a synthetic resin of the acrylic, vinyl, silicon, polymethylmethacrylate (PMMA), polyethylene or polyamide types of resin.

In accordance with a preferred embodiment of the invention, the matrix constitutes a printing ink which can be deposited on the document to be authenticated by any known means, in particular by conventional printing using a rubber stamp or a stylograph.

In accordance with another embodiment, the matrix constitutes a film with a small thickness, on the order of 5 to 20 $\mu$m, which is applied on at least one part of the object to the authenticated by transfer, coating or any other known printing method.

In accordance with another embodiment of the invention, the matrix constitutes a semi-rigid sheet of the credit card type.

In accordance with one embodiment of the present invention, the matrix incorporating the dopants constitutes small-sized particles. These particles are intended to be incorporated in the material constituting the fiduciary object.

These particles can be in the form of grains, pellets or fibers and are produced in doped synthetic resin in accordance with the present invention. The size of these particles is on the order of about 10 micrometers for the cross-section of the grains or pellets and on the order of a few millimeters for the length of the fibers or the diameters of the pellets. These particles are included in the material constituting the fiduciary object at the time of the preparation of said material.

In the case of a fiduciary object of the banknote, title or fiduciary paper type, the particles are introduced into the paper pulp at the time of preparation of the paper.

The doping materials are photoluminescent cyclic aromatic compounds or doped crystals, in particular tungstate or sulfides doped with heavy metals such as Cu, Co, Mn, Ag, Bi, Eu, Tb, etc.

By way of indication, good results are obtained using the following dopants:

diphenyloxazol (PPO), crystals of calcium and strontium sulfide doped with bismuth, crystals of zinc and cadmium sulfide doped with copper, crystals of zinc sulfide doped with copper, crystals of yttrium oxysulfide doped with europium ($Y_2$, $O_2$, S, Eu), derivatives of the xanthene, acridine, chinoline, thiazole, indamine, quinone or ketone types, and preferably derivatives of the indanthrene type.

Of course, numerous other photoluminescent crystals and/or photoluminescent cyclic aromatic compounds can be used.

The verification of the authenticity of an object marked in accordance with the invention is carried out by a study of the daytime color, of the color re-emitted when the document is subjected to ultraviolet radiation and the remanence color when the object is observed in darkness, after having been exposed to visible or ultraviolet radiation, for example, to daylight.

This verification can be carried out by visual observation or automatically by means of a device subjecting the document to be verified successively to radiation in the visible spectrum, to ultraviolet radiation and to darkness, and analyzing the chromatic response of the object using electronic sensors.

In accordance with an alternative of the present invention, the dopants or the doped matrix are coated with a substance which is transparent to radiation having a wavelength between infrared and ultraviolet, except for at least a given narrow spectral band.

This non-transparent band is selected so as to be included in the absorption band of one of the doping materials.

In accordance with an example of a preferred embodiment, this non-transparent band is centered on a wavelength of 255 nanometers or 366 nanometers, corresponding to the wavelengths of lamps within the ultraviolet waveband normally used for the verification of fiduciary documents.

In this manner, different behavior is obtained in the case of illumination with one or other types of ultraviolet lamp.

Of course, this non-transparent band can be centered on wavelengths corresponding either to the visible spectrum or to the ultraviolet wavebands.

The substance is composed of an organic resin of a known type, for example a nickel-based organic resin.

A substance of the 2, 5, $2^{IV}$, $5^{IV}$ tetramethyl-p-quinque-phenyl type can be used which has transparency in the visible and ultraviolet spectra, except for an absorption band between 240 nanometers and 320 nanometers, or a substance of the 4, 6 dimethyl 7 ethylamino-coumarin type which is transparent in the visible and ultraviolet spectra, except for a band between 340 nanometers and 400 nanometers, or even substances of the 3, 5, $3^{IV}$, $5^{IV}$ tetra-t-butyl-p-quinquephenyl type whose absorption band is between 280 nanometers and 340 nanometers.

Said substance is deposited on the crystalline dopants or the doped matrix in the form of particles (grains, pellets, fibers) or of a film by coating or by tempering in a bath of the organic substance.

Other characteristics and advantages will become more apparent from the following description which refers to the single drawing showing the graph of absorption and re-emission of an example of an embodiment of the invention.

On the single drawing, the wavelengths are shown in abscissa in angstroms and the absorption and re-emission coefficient in ordinates which are respectively positive and negative.

Line (1) corresponds to a dopant of the PPO type. It is noted that the re-emission band corresponds to the absorption bands of two other dopants of the zinc sulfide crystals doped with copper type (line (2)) and indanthrene (line (3)) for the example shown on this drawing, and causes a phenomena of "light cascade". The role of the PPO or of any other dopant having an absorption band in the ultraviolet and a re-emission band corresponding substantially to the absorption band of at least one of the other photoluminescent doping materials is to assist the working of the other dopants by a "light cascade" effect.

Line (4) corresponds to a dopant with long-lasting remanence of the calcium and strontium sulfide crystals doped with bismuth type in the example shown in the single drawing.

The behavior of the fiduciary object will be the following: when the document is submitted to daylight, it appears with a first shade corresponding to the natural color of the dopants; when the document is submitted to ultraviolet radiation, it appears with a shade corresponding to the re-emission band or bands of the dopants or the light cascades; when the document is replaced in darkness, it shows a third shade coming from the long-lasting remanence.

In the following description, by way of indication four examples of embodiments will be present which in no way restrict or limit the scope of the present invention.

EXAMPLE 1

This example relates to the preparation of one kilogram of finished product. A typical composition is obtained as follows: at a moderate temperature and using known techniques, 5 grams of fluorescent dopant of the indanthrene type, 300 grams of zinc sulfide crystals doped with copper and 0.1 gram of PPO are dissolved in 400 grams of vinyl or acrylic resin. The document marked with the composition of this example will have a pink color in daylight, a green color when submitted to ultraviolet radiation and a blue long-lasting remanence in darkness.

EXAMPLE 2

For the preparation of one kilogram of finished product, a typical composition is obtained as follows: 5 grams of fluorescent dopant of the indanthrene type, 300 grams of zinc and cadmium sulfide crystals doped with copper, 300 grams of yttrium oxysulfide crystals doped with europium and 0.1 gram of PPO are dissolved in 400 grams of acrylic or vinyl resin. The document marked in accordance with this example will have a greenish tint in daylight, a red tint when the document is exposed to ultraviolet radiation, and a orangish tint in darkness from long-lasting remanence.

EXAMPLE 3

For the preparation of one kilogram of finished product, a composition is obtained as follows: 5 grams of fluorescent dopant of the indanthrene type, 200 grams of yttrium oxysulfide crystals doped with europium, 300 grams of zinc sulfide crystals doped with copper and 0.1 gram of PPO are dissolved in 400 grams of acrylic or vinyl resin. The document marked with the composition in accordance with this example will have a pale blue color in daylight, an orangish red color upon exposure to ultraviolet radiation, and a pale green color in darkness.

EXAMPLE 4

For the preparation of one kilogram of finished product, a typical composition is obtained as follows: 300 grams of yttrium oxysulfide doped with europium, 300 grams of zinc sulfide crystals doped with long remanence copper and 0.1 gram of PPO are dissolved in 400 grams of polymethacrylate resin. The product obtained in this manner will be prepared in the form of grains having an average cross-section of 8 micrometers. These grains are incorporated into the paper pulp. The sheet of paper obtained in this manner will further be coated with a resin containing a substance of the 2, 5, $2^{IV}$, $5^{IV}$ tetramethyl-p-quinquephenyl type forming an anti-ultraviolet mask for the wavelength band including the wavelength of 255 nanometers which is normally used for ultraviolet response tests. The document marked with a composition in accordance with this composition will have a greenish white tint in daylight, an orangish red color during exposure to ultraviolet radiation and will be green in darkness. However, the orangish red response will not be obtained if the document marked in accordance with this example is examined using an ultraviolet source principally emitting in the wavelengths close to 255 nanometers.

What is claimed is:

1. A fiduciary or security object having optical characteristics enabling its identification and rendering difficult its reproduction, comprising on at least one part, an organic matrix selected from the group consisting of resins of the acrylic, vinyl, silicon, polymethylmethacrylate (PMMA), polyethylene and polyamide types; incorporating in said organic matrix at least one sparkling doping material with short remanence and at least one photoluminescent doping material with long-lasting remanence forming a light cascade which absorbs solar radiation and re-emits radiation at a first predetermined wavelength, absorbs an ultraviolet radiation and re-emits, radiation at a second predetermined wavelength, and, after exposure to said radiation, emits radiation at a third predetermined wavelength, said doping materials being selected from the group consisting of photoluminescent cyclic aromatic compounds and crystals of sulfide or tungstate doped with one element selected from the group consisting of copper, cobalt, manganese, silver, bismuth, europium and terbium--.

2. The object in accordance with claim 1 wherein the first, second and third re-emission wavelengths are situated in the spectrum of visible or close infrared light.

3. The object in accordance with claim 1, wherein said organic matrix is covered with a substance which is transparent in the spectral band going from ultraviolet to infrared, except for at least one given wavelength band.

4. The object in accordance with claim 3 wherein said substance is transparent in the spectral band going from ultraviolet to infrared, except for a wavelength band including the wavelength of 255 nanometers.

5. The object in accordance with claim 3, wherein said substance is transparent in the spectral band going from ultraviolet to infrared, except for a wavelength band including the wavelength of 366 nanometers.

6. The object in accordance with claim 1, wherein said organic matrix contains the following three doping materials:
   first doping material: substance of the indanthrene type
   second doping material: calcium and strontium sulfide crystals doped with bismuth
   third doping material: zinc sulfide crystals doped with copper.

7. The object in accordance with claim 1, wherein said organic matrix contains the following three doping materials:
   first doping material: substance of the indanthrene type
   second doping material: zinc and cadmium sulfide crystals doped with copper
   third doping material: yttrium oxysulfide crystals doped with europium.

8. The object in accordance with claim 6, wherein the amounts by weight of the doping materials are the following:
   first doping material: 0.5%
   second doping material: 30.0%
   third doping material: 30.0%
   bonding resin: 39.5%
with the totality being incorporated into a matrix doped with diphenyloxazol in an amount of approximately 0.04% by weight.

9. The object in accordance with claim 6, characterized in that it contains a fourth doping material of the PPO type in an amount of approximately 0.1 g/kg of finished product, and which is intended to assist the working of the other doping materials.

10. The object in accordance with claim 1, wherein said doped matrix is in the form of a film having a thickness on the order of 5 to 20 $\mu$m applied on at least one part of the object.

11. The object in accordance with claim 10, wherein said film is a transfer applied film.

12. The object in accordance with claim 1, wherein said matrix is one material from the group consisting of a varnish and a printing ink.

13. The object in accordance with claim 12, wherein said matrix is a coated varnish.

14. The object in accordance with claim 1, wherein said doped matrix is in the form of particles incorporated in the components of the object.

15. The object in accordance with claim 14, wherein said particles are incorporated in paper.

* * * * *